United States Patent
Krumsiek

(10) Patent No.: US 9,572,634 B2
(45) Date of Patent: Feb. 21, 2017

(54) DENTAL INSTRUMENT

(75) Inventor: Michael Krumsiek, Lemgo (DE)

(73) Assignee: Gebr. Brasseler GmbH & Co. KG, Lemgo (DE)

(*) Notice: Subject to any disclaimer, the term of this patent is extended or adjusted under 35 U.S.C. 154(b) by 0 days.

(21) Appl. No.: 13/369,081

(22) Filed: Feb. 8, 2012

(65) Prior Publication Data

US 2012/0208147 A1 Aug. 16, 2012

(30) Foreign Application Priority Data

Feb. 10, 2011 (DE) .......................... 10 2011 010 897

(51) Int. Cl.
| | |
|---|---|
| *A61C 3/06* | (2006.01) |
| *A61C 3/02* | (2006.01) |
| *B23B 31/00* | (2006.01) |
| *B23C 5/10* | (2006.01) |

(52) U.S. Cl.
CPC .............. *A61C 3/02* (2013.01); *B23B 31/005* (2013.01); *B23C 5/10* (2013.01)

(58) Field of Classification Search
CPC ............ B23C 2210/02; B23C 2210/03; B23C 2240/32; A61C 3/06; B23B 2251/02; B23B 2240/21
USPC ......... 433/3, 102, 165, 166; 29/428; 407/30, 407/32, 53, 54, 12–19, 23; 408/199–233; 606/80–81, 180, 169–172; 132/73.6, 132/75.6; 76/115; 451/541; 422/37, 274
See application file for complete search history.

(56) References Cited

U.S. PATENT DOCUMENTS

| | | | | |
|---|---|---|---|---|
| 170,178 | A | * | 11/1875 | Locke et al. .................. 451/512 |
| 1,191,717 | A | * | 7/1916 | Moore .......................... 408/144 |
| 2,086,133 | A | * | 7/1937 | Kennedy ...................... 285/349 |
| 2,177,100 | A | * | 10/1939 | Frame ........................... 285/334 |
| 2,380,690 | A | * | 7/1945 | Graham ........................ 285/114 |
| 2,506,477 | A | * | 5/1950 | Warren, Jr. ................... 411/223 |
| 2,695,452 | A | * | 11/1954 | Christian ...................... 433/165 |
| 2,942,640 | A | * | 6/1960 | Lundeberg .................... 411/302 |
| 3,002,770 | A | * | 10/1961 | Chesnut et al. ................ 285/94 |
| 3,047,316 | A | * | 7/1962 | Wehring et al. .............. 285/334 |
| 3,142,138 | A | * | 7/1964 | Kean et al. ................... 451/541 |

(Continued)

FOREIGN PATENT DOCUMENTS

| | | |
|---|---|---|
| DE | 102004047909 | 4/2006 |
| DE | 102006049581 | 4/2008 |

(Continued)

OTHER PUBLICATIONS

Translation of WO20110006804.*

(Continued)

*Primary Examiner* — Nicholas Lucchesi
*Assistant Examiner* — Matthew Saunders
(74) *Attorney, Agent, or Firm* — Shuttleworth & Ingersoll, PLC; Timothy J. Klima

(57) ABSTRACT

A dental instrument includes a head (2) having cutting edges (1) and made of a ceramic material, and a shaft (3) which can be clamped into a driving member and is made of a metal material. The head (2) includes a mounting plug (4) having an external thread (5) and the shaft (3) includes a front-side threaded recess (6) into which the mounting plug (4) can be screwed. At least one locking recess is formed between the mounting plug (4) and the threaded recess (6).

20 Claims, 2 Drawing Sheets

(56) References Cited

U.S. PATENT DOCUMENTS

Figure 1:
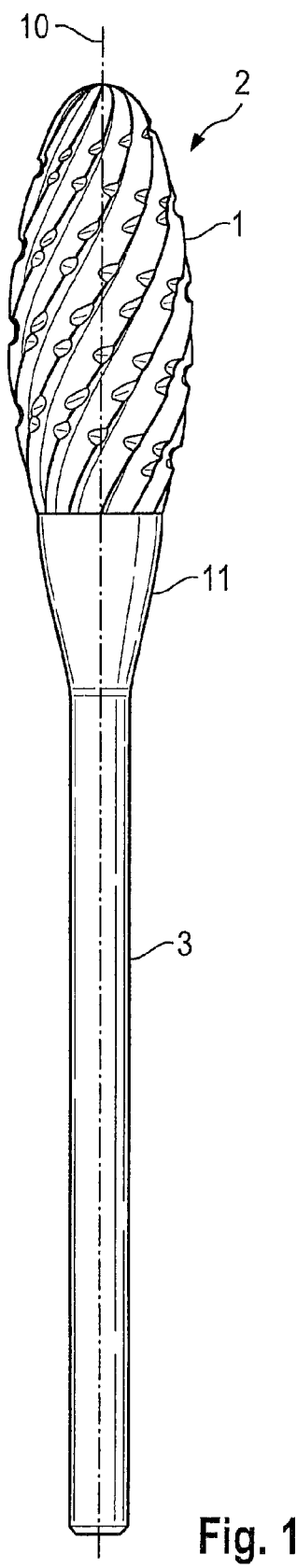

| | | | |
|---|---|---|---|
| 3,339,003 A * | 8/1967 | Cessna | 264/262 |
| 3,414,034 A * | 12/1968 | Imse | 411/304 |
| 3,566,947 A * | 3/1971 | Jukes | 411/260 |
| 3,687,493 A * | 8/1972 | Lock et al. | 285/333 |
| 3,850,054 A * | 11/1974 | Weissman | 76/108.1 |
| 3,879,071 A * | 4/1975 | Gockler | 285/347 |
| 4,011,121 A * | 3/1977 | Doss | 156/82 |
| 4,828,294 A * | 5/1989 | Bounie et al. | 285/334 |
| 4,828,295 A * | 5/1989 | Plaquin et al. | 285/334 |
| 5,028,162 A * | 7/1991 | Tsuno et al. | 403/30 |
| 5,106,130 A * | 4/1992 | Ellsworth et al. | 285/355 |
| 5,114,286 A * | 5/1992 | Calkins | 408/226 |
| 5,407,312 A | 4/1995 | Terrizzi | |
| 5,496,137 A | 3/1996 | Ochayon et al. | |
| 5,598,751 A * | 2/1997 | Ochayon et al. | 76/108.6 |
| 5,971,670 A * | 10/1999 | Pantzar et al. | 407/34 |
| 6,106,291 A | 8/2000 | Boston | |
| 6,565,291 B2 * | 5/2003 | Harpaz et al. | 407/53 |
| 7,473,049 B2 * | 1/2009 | Holowczak et al. | 403/272 |
| 7,611,311 B2 * | 11/2009 | Kakai et al. | 407/54 |
| 7,887,354 B2 * | 2/2011 | Holliday | 439/321 |
| 2006/0062642 A1 | 3/2006 | Jonsson et al. | |
| 2006/0105296 A1 * | 5/2006 | Linder et al. | 433/173 |
| 2006/0127847 A1 * | 6/2006 | Danger et al. | 433/165 |
| 2009/0170053 A1 * | 7/2009 | Ikemi | 433/166 |
| 2010/0151421 A1 * | 6/2010 | Devengencie et al. | 433/174 |
| 2010/0248182 A1 * | 9/2010 | Sonoi et al. | 433/166 |
| 2010/0319492 A1 * | 12/2010 | Smith et al. | 76/108.4 |

FOREIGN PATENT DOCUMENTS

| | | | | |
|---|---|---|---|---|
| DE | 102010015934 A1 * | 9/2011 | | B23B 51/12 |
| GB | 1458886 | 12/1976 | | |
| WO | WO 2011006804 A2 * | 1/2011 | | B23B 31/1107 |

OTHER PUBLICATIONS

Translation of DE 10 2010 015 934 A1.*
Office Action from counterpart German application dated Sep. 29, 2011.
European Search Report dated Apr. 7, 2015 for counterpart European Application No. EP12000008.

* cited by examiner

DENTAL INSTRUMENT

This application claims priority to German Patent Application DE102011010897.1 filed Feb. 10, 2011, the entirety of which is incorporated by reference herein.

The invention relates to a dental instrument comprising a head provided with cutting edges as well as a shaft which can be clamped into a driving member.

In detail, the invention relates to a dental instrument in which the head is made of a ceramic material and the shaft is made of a metal material.

In detail, the invention in particular refers to a milling tool which is specifically used in dental technology laboratories. However, the invention is not limited thereto. Also the use in general surgery, for example to avoid artefacts in imaging by a MRT during the treatment, is conceivable.

From the state of the art, it is known to manufacture such dental instruments either completely of metal or completely of plastics. In case of embodiments in which the head has a larger diameter and/or larger dimensions than the shaft, it is undesirable that an excessive amount of material has to be removed from the blank in the region of the shaft, in particular when manufacturing the instruments from a ceramic material, due to economic reasons as well as for reasons of precise manufacturing. Therefore, so-called hybrid dental instruments were developed, in which the head is made of a ceramic material, whereas the shaft is made of metal and in which the ceramic head is joined to the metal shaft. Such joints, however, require a secure connection which is not disconnected by the forces and/or vibrations occurring during the use of the instrument.

The object underlying the invention is to provide a dental instrument of the aforementioned type which comprises a non-detachable connection between the head and the shaft, while having a simple structure and being manufactured simply and at low costs.

According to the invention, it is thus provided that the head includes a mounting plug which is provided with an external thread. Such a mounting plug can be manufactured easily from a ceramic material, e.g. by grinding. As a result, low manufacturing costs are achieved on the one hand, and on the other hand, it is possible to configure the mounting plug as well as the thread such that a secure connection and a good force transmission results, and a construction can be chosen which decreases the danger of notch stress or the like.

According to the invention, it is provided that the shaft has a threaded recess at its front end portion, into which the mounting plug can be screwed. Also the production of the shaft including the threaded recess can be realized easily and at low costs, in particular by a machining process.

According to the invention, it is further provided that a locking recess is formed in the region between the mounting plug and the threaded recess.

In a particularly preferred embodiment of the invention, it is provided that the locking recess is configured such that it is suited for inserting a form-fit locking member. With the help of the inventive locking member, a relative rotation between the two threads of the mounting plug and the treaded recess is prevented. Consequently, it is excluded that the head detaches from the shaft due to forces, vibrations and the like occurring during the operation of the dental instrument.

In particular, the invention provides that the locking member is arranged such that it engages with at least a recess of the threaded recess and/or of the mounting plug in a form-fit manner to prevent rotation.

According to the invention, the locking member is made of a curable material which is preferably flexible, liquid or pasty prior to curing. In particular, the inventive locking member can be made of an adhesive material.

As an alternative, the locking member can also be realized by an active solder which is then heated inductively through the steel shaft fitted into the ceramic head.

The production of the inventive dental instrument is thus performed by first forming the external thread at the mounting plug and the threaded recess, after having manufactured the head and the shaft either as a blank or already having their final shape. Subsequently, the external thread of the mounting plug is screwed into the threaded recess, wherein the locking member is applied. The application of the locking member can be performed, e.g. when using a pasty, liquid or flexible locking member, such that the material of the locking member is applied onto the external thread and/or introduced into the threaded recess. Upon a subsequent screwing of the mounting plug into the threaded recess, the material of the locking member is thus squeezed between the thread pitches and is additionally introduced into the at least one locking recess. After curing the material of the locking member, such material connects the external thread of the mounting plug to the threaded recess. In addition, further contact surfaces between the head and the shaft can be glued or connected. Since the material of the locking member is particularly introduced into the locking recess, a form-fit anchoring is achieved, which prevents a relative rotation between the external thread and the thread of the threaded recess. Even in case of a disassociation of the contact or the adhesion between the material of the locking member and the external thread of the mounting plug or the thread of the threaded recess, no relative rotation may occur due to the form-fit anchoring. Therewith, the head cannot detach from the shaft.

The inventive anti-rotation device does not require a thick and voluminous configuration of the locking member. Rather, the two threads can be glued in a usual manner, wherein small amounts of adhesive are sufficient for this joint connection. It is essential that the locking recess is provided, which is filled with the material of the locking member and in which a solid locking member is thus formed after curing.

In a preferred embodiment of the invention, it can be provided to have a clearance between the thread of the mounting plug and the internal thread of the threaded recess, in order to introduce material for the locking member.

The locking recess is preferably formed as an annular groove arranged in the threaded recess, however, it is also possible to provide recesses directed in the axial direction, such as grooves or bevels. According to the invention, it is essential that a closed internal volume is present which is filled with the material of the locking member while the mounting plug is screwed into the threaded recess. Due to the subsequent curing of the material of the locking member, there results the inventive form-fit anchoring.

In a preferred embodiment of the invention, it is further provided that the mounting plug and/or the threaded recess includes a decompression recess. Such recess is preferably arranged axially (with respect to the center axis of the dental instrument). The decompression recess discharges excessive material of the locking member during the screwing step. Since the material of the locking member is non-compressible, there results a secure connection between the head and the shaft.

In a preferred embodiment of the invention, it is possible to form the decompression recess as the locking recess since also a decompression groove extending e.g. in the axial direction, after being filled with the material of the locking member and cured, prevents a relative rotation between the external thread of the mounting plug and the internal thread of the threaded recess in a form-fit manner.

According to the invention, adhesives are particularly used as the material of the locking member, which adhesives have a bio-compatibility pursuant to DIN EN ISO 10993.

It is obvious that the invention is not restricted to the construction of a mounting plug having an external thread at its head and a threaded recess at its shaft. Rather, it is also possible according to the invention to provide a threaded recess in the head and the mounting plug at the shaft.

The threads provided according to the invention can be of most different configurations, e.g., they can be single threads or multi threads. The basic shape of the mounting plug as well as of the threaded recess can be cylindrical or conical. Further, it is preferred that the thread is formed as a round thread. Therewith, notch stress is prevented. Further, different thread leads can be provided according to the invention.

Figure 2:
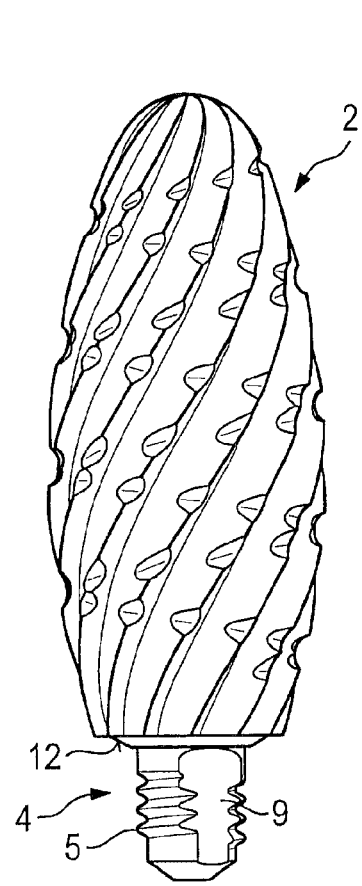
Figure 2:
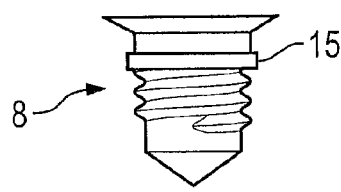
Figure 2:
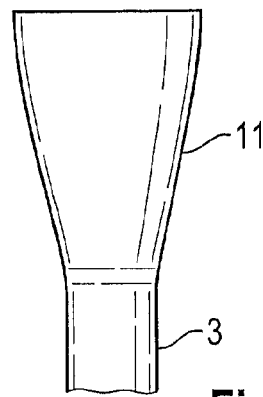
Figure 3:
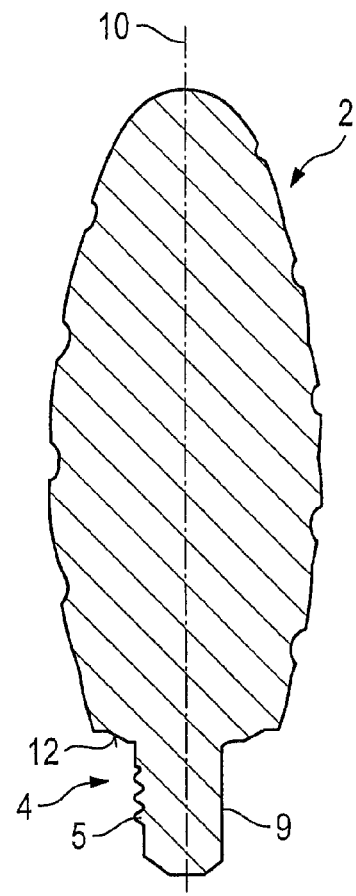
Figure 3:
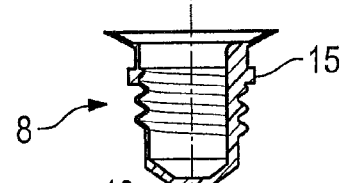
Figure 3:
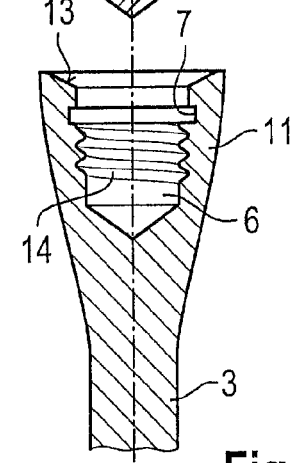

In the following, the invention is described on the basis of an embodiment in connection with the drawing, in which FIG. 1 shows a lateral view of an inventive dental instrument in the finished state, FIG. 2 shows an exploded view, and FIG. 3 shows a sectional view analogous to FIG. 2

The inventive dental instrument includes a cylindrical metal shaft 3 which is configured and dimensioned in the usual manner. The shaft 3 can be clamped into a driving device, e.g. an angle piece. At its end portion, the shaft 3 is connected to a connection portion 11 having an enlarged diameter. A head 2 made of a ceramic material is attached at the connection portion 11 of the shaft 3. The head 2 can be configured in the usual manner, as is shown in the state of the art. The head 2 comprises a plurality of cutting edges 1; it may have a cylindrical, rounded, spherical, crowned or any other shape. Reference numeral 10 designates the center axis/rotary axis.

FIGS. 2 and 3 show a schematic exploded view, wherein the head 2 is shown as a cylindrical blank which not yet has its final shape including the cutting edges 1, as shown in FIG. 1.

A mounting plug 4 is formed at the head 2, which mounting plug basically has a cylindrical shape and is provided with an external thread 5. The external thread 5 may e.g. be designed as a round thread.

Adjacent to the mounting plug 4, a contact surface 12 is formed which is shaped as a cone and is formed to match with a contact surface 13 of the connection portion 11 of the shaft 3. Therewith, there results a sealing abutment between the head 2 and the shaft 3, such that a jointless connection (in particular by gluing) is possible.

As is discernible from FIG. 3, the shaft 3 includes a threaded recess 6 which is formed to match with the external thread 5.

For providing the inventive anti-rotation device, a locking recess 7 is formed in the region of the internal thread of the threaded recess 6, which is formed as an undercut annular groove.

FIGS. 2 and 3 further show a locking member 8 which is formed by introducing a curable material when screwing the external thread 5 into a thread 14 of the threaded recess 6. For this purpose, e.g. a curable adhesive is introduced into the threaded recess 6 or applied onto the mounting plug 4. Upon screwing, this material forming the locking member 8 is squeezed into the resulting clearances and remains in the resulting clearances after curing, in particular into the locking recess 7. Thus, a locking member 8 is formed, as it is shown in FIGS. 2 and 3.

According to the invention, a decompression recess 9 is provided which can be formed e.g. as a bevel or an axial groove of the mounting plug 4. Therewith, excessive material (adhesive) of the locking member is extruded.

It is obvious that the locking member 8 shown in FIGS. 2 and 3 does not inevitably have to be formed in this body shape. It is sufficient if the locking recess 7 (undercut, annular groove etc.) is completely filled with the material of the locking member. In the shown embodiment, the locking member 8 forms an annular bead 15 which is located in the annular groove 7 (locking recess) and prevents axial motion of the locking member 8 and head 2. Depending on the clearance between the external thread 5 of the mounting plug 4 as well as the dimensions of the threaded recess 6, there may result additionally the cap-shaped or cup-shaped configuration shown in FIGS. 2 and 3. In total, it is essential according to the invention that a form-fit locking member preventing a detaching rotation is provided in the contact area between the external thread 5 of the mounting plug 4 and the internal thread 14 of the threaded recess 6.

The material of the locking member can be a multi-component material, which is self-curing. However, it is also possible to use a material which can be cured e.g. by heat. Also a material which can be liquefied by heat, e.g. a solder material, can be used according to the invention.

According to the invention, a connection between the head and the shaft is thus performed by using an adhesive material as the material for the locking member by a common gluing by adhesion or the like. The inventive form-fit locking member serves to prevent an unscrewing and detaching of the thread in a case that the adhesive connection (joint connection) should disassociate by occurring forces or vibrations, due to temperature effects or other effects.

LIST OF REFERENCE NUMERALS 1 cutting edge
2 head
3 shaft
4 mounting plug
5 external thread
6 threaded recess
7 locking recess/undercut/annular groove
8 locking member
9 decompression recess
10 center axis/rotary axis
11 connection portion
12 contact surface
13 contact surface
14 thread
15 annular bead

The invention claimed is:
1. A dental instrument, comprising:
a head having cutting edges and made of a ceramic material, the head including a mounting plug having an external thread, the head including a first contact surface;
a shaft which can be clamped into a driving member and is made of a metal material, the shaft including a front-side threaded recess having an internal thread, the front-side threaded recess having an open end facing away from a center of the shaft and a bottom end positioned away from the open end, the shaft including a second contact surface for engaging the first contact surface;

the mounting plug including a decompression recess extending axially with respect to a center axis of the dental instrument, the decompression recess having a portion having a decompression recess inner radius which is bounded on both circumferential sides by portions of the plug having at least a decompression recess outer radius greater than the decompression recess inner radius;

a locking recess positioned in the shaft such that at least a portion of the threaded recess is positioned between the locking recess and the bottom end with the locking recess interrupting the internal thread before reaching the front side of the shaft, wherein the locking recess includes at least one of an undercut or an annular groove; the locking recess positioned in the shaft and having a locking recess extending portion extending radially outwardly of the threaded recess to a locking recess outer radius, the locking recess axially bounded on a side toward the open end by a locking face of the shaft which extends radially inwardly to a locking recess inner radius positioned radially inwardly of the locking recess outer radius;

a locking member including an externally threaded portion and an internally threaded portion, the externally threaded portion of the locking member threadingly engaging the internal thread of the shaft and the internally threaded portion of the locking member threadingly engaging the external thread of the head, the locking member also including a locking member outward extending portion radially extending into the locking recess extending portion to a radial position radially outwardly of the locking recess inner radius to be positioned in the locking recess and engage the locking recess, the locking face of the shaft blocking an axial movement of the locking member outward extending portion in an outward direction toward the open end to prevent outward axial movement of the locking member with respect to the locking recess, the locking member having a locking member inward extending portion extending radially inwardly toward the decompression recess to a position radially inwardly of the decompression recess outer radius, to thereby engage the decompression recess and rotationally block the portions of the plug having the at least decompression recess outer radius to prevent rotation of the locking member with respect to the decompression recess, the engagement of the locking member between the locking recess and the decompression recess preventing rotation and detachment of the head from the shaft;

the locking member having a radially overlapping engagement with the mounting plug to prevent axial movement between the mounting plug and the locking member, and via the engagement between the locking member and the locking recess, prevent axial movement between the mounting plug and the shaft;

wherein the locking member consists of a curable material cured in place between the head and the shaft to form a rigid, non-compressible, permanent bond between the head and the shaft.

2. The dental instrument of claim 1, wherein the curable material is at least one chosen from a flexible material, liquid material, pasty material, adhesive material and a material that can be transferred from a liquid state to a solid state.

3. The dental instrument of claim 2, and further comprising a clearance positioned between the mounting plug and the threaded recess.

4. The dental instrument of claim 3, wherein the locking recess is an annular groove disposed in the threaded recess.

5. The dental instrument of claim 4, and further comprising at least one of a groove or a bevel formed at the mounting plug.

6. The dental instrument of claim 5, wherein at least one of the thread of the mounting plug or the thread of the threaded recess is formed as at least one of a round thread, a single thread, a multi thread, in a generally cylindrical shape, or in a generally conical shape.

7. The dental instrument of claim 1, wherein at least one of the thread of the mounting plug or the thread of the threaded recess is formed as at least one of a round thread, a single thread, a multi thread, in a generally cylindrical shape, or in a generally conical shape.

8. The dental instrument of claim 1, wherein the radially overlapping engagement is formed by an engagement between a threaded portion of the mounting plug and a corresponding threaded portion of the locking member.

9. The dental instrument of claim 1, wherein the locking recess interrupts the internal thread around an entire circumference of the internal thread.

10. The dental instrument of claim 9, wherein the engagement of the first contact surface with the second contact surface forms a sealing abutment between the head and the shaft.

11. The dental instrument of claim 10, wherein at least one chosen from the first contact surface and the second contact surface is at least partially conically shaped.

12. The dental instrument of claim 11, wherein there is only a single locking member inward extending portion and a single decompression recess.

13. The dental instrument of claim 10, wherein there is only a single locking member inward extending portion and a single decompression recess.

14. The dental instrument of claim 1, wherein the engagement of the first contact surface with the second contact surface forms a sealing abutment between the head and the shaft.

15. The dental instrument of claim 14, wherein at least one chosen from the first contact surface and the second contact surface is at least partially conically shaped.

16. The dental instrument of claim 15, wherein there is only a single locking member inward extending portion and a single decompression recess.

17. The dental instrument of claim 16, wherein there is only a single locking member inward extending portion and a single decompression recess.

18. The dental instrument of claim 1, wherein at least one chosen from the first contact surface and the second contact surface is at least partially conically shaped.

19. The dental instrument of claim 18, wherein there is only a single locking member inward extending portion and a single decompression recess.

20. The dental instrument of claim 1, wherein there is only a single locking member inward extending portion and a single decompression recess.

* * * * *